(12) United States Patent
Inagaki et al.

(10) Patent No.: US 8,030,486 B2
(45) Date of Patent: Oct. 4, 2011

(54) SUCCINIC ACID DIESTER DERIVATIVE, PROCESS FOR PRODUCTION THEREOF, AND USE OF THE DERIVATIVE IN THE PRODUCTION OF PHARMACEUTICAL PREPARATION

(75) Inventors: Takashi Inagaki, Hirakata (JP); Yoshikazu Yamakawa, Hirakata (JP)

(73) Assignees: Dainippon Sumitomo Pharma Co., Ltd., Osaka (JP); Katayama Seiyakusyo Co., Ltd., Osaka (JP)

( * ) Notice: Subject to any disclaimer, the term of this patent is extended or adjusted under 35 U.S.C. 154(b) by 0 days.

(21) Appl. No.: 12/938,618

(22) Filed: Nov. 3, 2010

(65) Prior Publication Data

US 2011/0046373 A1 Feb. 24, 2011

Related U.S. Application Data

(62) Division of application No. 12/310,524, filed as application No. PCT/JP2007/066862 on Aug. 30, 2007.

(30) Foreign Application Priority Data

Aug. 31, 2006 (JP) .................................. 2006-234777

(51) Int. Cl.
C07D 241/38 (2006.01)
(52) U.S. Cl. ...................................... 544/230
(58) Field of Classification Search .................. None
See application file for complete search history.

(56) References Cited

U.S. PATENT DOCUMENTS 5,258,382 A 11/1993 Negoro et al.

FOREIGN PATENT DOCUMENTS

| JP | 5-186472 | 7/1993 |
| JP | 6-192222 | 7/1994 |
| JP | 8-176105 | 7/1996 |

OTHER PUBLICATIONS

Mashiko et al. J. Am. Chem. Soc. (2007), vol. 129, pp. 11342-11343.*

International Search Report dated Oct. 16, 2007 in the International (PCT) Application PCT/JP2007/066862 of which the parent application is the U.S. National Stage.
Toshiyuki Negoro et al., "Novel, Highly Potent Aldose Reductase Inhibitors: (R)-(—)-2-(4-Bromo-2-fluorobenzyl)-1,2,3,4-tetrahydropyrrolo[1,2-a]pyrrazine-4-spiro-3'-pyrrolidine-1,2',3,5'-tetrone (AS-3201) and Its Congeners", J. Med. Chem., 41, pp. 4118-4129, 1998.
Supplementary European Search Report issued Mar. 4, 2010 in corresponding European Application No. 07 80 6339, in the English language.
XP-002568212, "AS-3201 Aldose Reductase Inhibitor", Drugs of the Future, 25 (2), pp. 131-136 (2000).

* cited by examiner

*Primary Examiner* — Kamal Saeed
*Assistant Examiner* — Nyeemah A Grazier
(74) *Attorney, Agent, or Firm* — Wenderoth, Lind & Ponack, L.L.P.

(57) ABSTRACT

The present invention provides with a process of preparing an optically active succinimide derivative, which is a key intermediate for production of ranirestat. A compound (3) is easily prepared by treating the derivative of succinic acid diester of the formula (2):

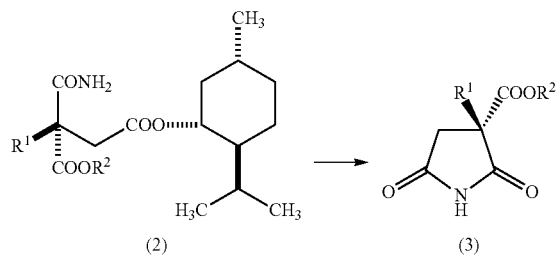

wherein $R^1$ is an amino group protected with a group removed by hydrogenolysis or a tert-butoxycarbonylamino group and $R^2$ is an ethyl group optionally substituted with one or two methyl group(s) at α-position, provided that $R^2$ is not a tert-butyl group when $R^1$ is a tert-butoxycarbonylamino group; with alkali metal alkoxide and the compound (3) can be an important intermediate for production of ranirestat.

2 Claims, No Drawings

SUCCINIC ACID DIESTER DERIVATIVE, PROCESS FOR PRODUCTION THEREOF, AND USE OF THE DERIVATIVE IN THE PRODUCTION OF PHARMACEUTICAL PREPARATION

This application is a Divisional of U.S. application Ser. No. 12/310,524, filed Feb. 27, 2009, which is a national stage application of International application No. PCT/JP2007/066862, filed Aug. 30, 2007.

TECHNICAL FIELD

The present invention is related to a derivative of succinic acid diester and a process of preparing the derivative, which is useful for synthesizing [(3R)-2'-(4-bromo-2-fluorobenzyl)spiro[pyrrolidine-3,4'(1'H)-pyrrolo[1,2-a]pyrazin e]-1',2,3',5 (2'H)-tetraone: AS-3201] (ranirestat) and a key intermediate thereof (an optically active succinimide derivative). Ranirestat is now under development as an agent for treating diabetes complications.

BACKGROUND ART

Process for preparing an optically active succinimide derivative, one of the key intermediate for ranirestat, is disclosed in JP 1994-192222A and J. Med. Chem., 41, 4118 (1998). The process is shown in the scheme below, wherein R is a benzyloxycarbonylamino group or a pyrrol-1-yl group:

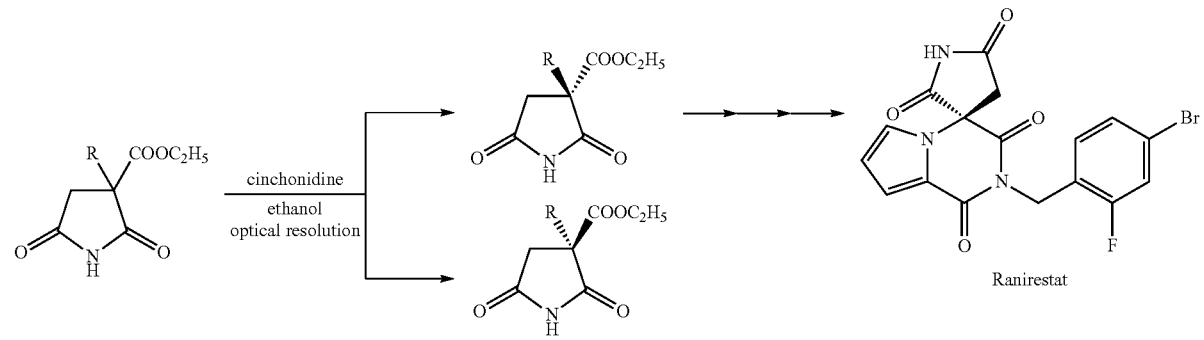

A sole process for preparing an optically active intermediate of ranirestat disclosed in JP1994-192222A and J. Med. Chem., 41, 4118 (1998) is an optical resolution method, in which a salt of racemic succinimide derivative with cinchonidine is crystallized.

JP1993-186472A discloses a process for preparing ranirestat shown in the scheme below,

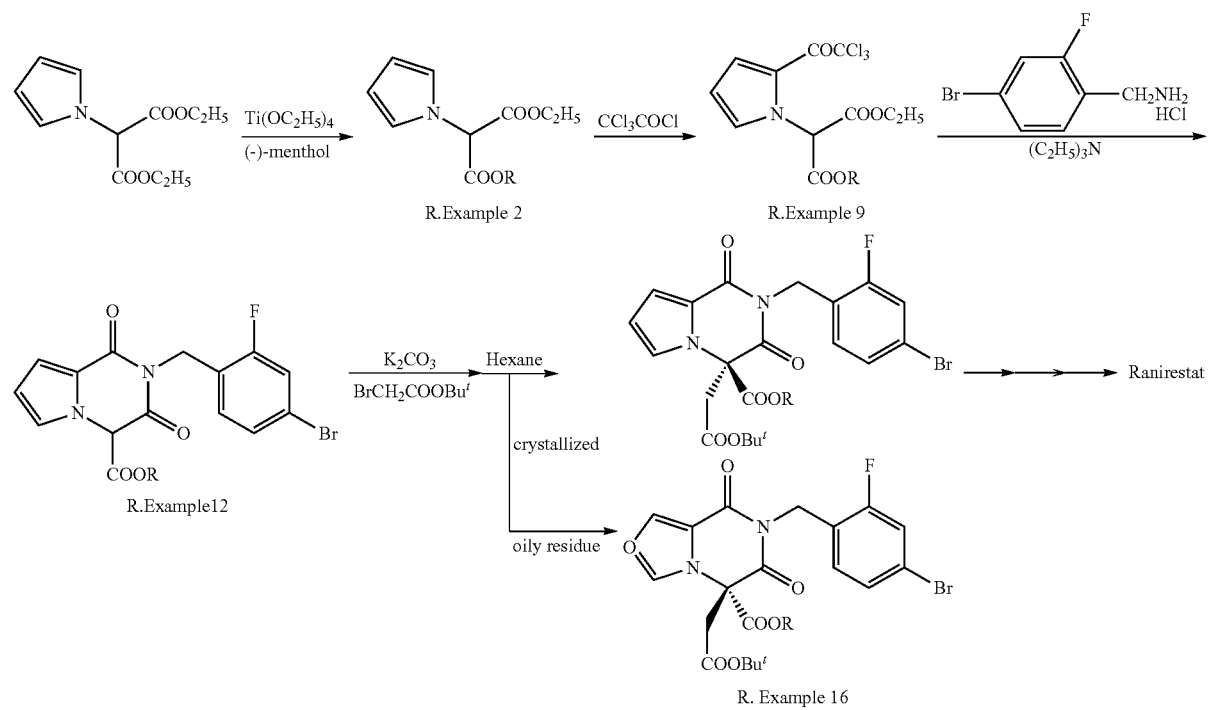

wherein R is a (−)-menthyl group.

In the process above, the optically active intermediate (a compound of Reference Example 16 in JP1993-186472A) was prepared from ethyl (−)-menthyl 2-(pyrrol-1-yl)malonate (a compound of Reference Example 2 in the said patent literature) through three steps. Each compound of the Reference Example 2 (oily product), the Reference Example 9 (oily product) and the Reference Example 12 (crystalline product) in JP1993-186472A is a diastereomeric mixture having (−)-menthyl ester as a partial structure, but all the (−)-menthyl ester are not always crystalline products or separation of the diastereomer is not always successful even if a crystalline product was obtained.

In the above patent literature for example, a diastereomer of (−)-menthyl ester is not isolated except the compound of Reference Example 16.

DISCLOSURE OF THE INVENTION

Problems to be Solved

In order to reduce the production costs of an optically active compound, it is preferred to carry out a procedure of optical resolution in an early process if possible.

Moreover, it would be a serious problem to utilize cinchonidine as an agent of optical resolution in a manufacturing process since it is a natural product obtained in an area with political instability, and stable price and/or supply are questionable. Utilization of an agent of optical resolution, which is available other than cinchonidine is extensively studied but successful reports could not be found at present. A new process for manufacturing a succinimide derivative without use of cinchonidine was therefore expected.

Means to Solve the Problem

The inventors have extensively studied synthetic intermediates which are suitable for production of the optically active succinimide derivative in a manufacturing scale and finally found a novel succinic acid diester derivative of the formula (1)(a compound of the present invention):

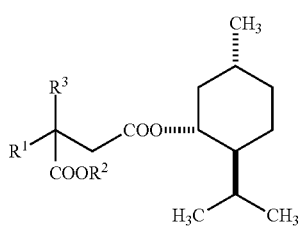

wherein $R^1$ is an amino group protected with a group removed by hydrogenolysis or a tert-butoxycarbonylamino group, $R^2$ is an ethyl group optionally substituted with one or two methyl group(s) at α-position, and $R^3$ is a cyano or carbamoyl group, provided that $R^2$ is not a tert-butyl group when $R^1$ is a tert-butoxycarbonylamino group; can solve the above mentioned problem; the compound (1) can be easily prepared from (−)-menthol which is commercially available in a large volume at low cost.

Specifically the inventors have found that the objective diastereomer could be preferentially produced when a compound of the formula (5) is reacted with (−)-menthyl chloroacetate, and that a diastereomer (2) having the preferred stereochemistry as an intermediate of ranirestat;

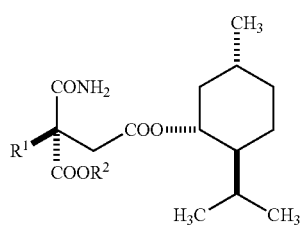

wherein $R^1$ is an amino group protected with a group removed by hydrogenolysis or a tert-butoxycarbonylamino group, and $R^2$ is an ethyl group optionally substituted with one or two methyl group(s) at α-position, provided that $R^2$ is not a tert-butyl group when $R^1$ is a tert-butoxycarbonylamino group; can be isolated as a crystal from the diastereomeric mixture (1a) if the cyano group of $R^3$ is converted to a carbamoyl group in the diastereomeric mixture.

In a compound wherein $R^2$ is a methyl or propyl group, an objective diastereomer is difficult to be isolated as a crystal and these are not practical intermediates of ranirestat.

The present invention also provides with a process for producing a succinimide derivative of the formula (3);

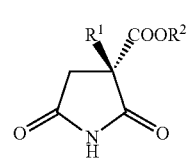

wherein $R^1$ is an amino group protected with a group removed by hydrogenolysis or a tert-butoxycarbonylamino group, and $R^2$ is an ethyl group optionally substituted with one or two methyl group(s) at α-position, provided that $R^2$ is not a tert-butyl group when $R^1$ is a tert-butoxycarbonylamino group, through an intramolecular cyclization reaction of the compound (2) under the presence of alkali metal alkoxide.

As the alkali metal alkoxide, sodium ethoxide is preferred and ethanol is preferably used as a reaction solvent.

In addition, the present invention provides with a process for producing ranirestat using the succinimide derivative (3) prepared by the method described above as a synthetic intermediate or a starting compound.

The present invention provides with a process for producing a succinic acid diester derivative of the formula (1b), which is a compound of the formula (1) wherein $R^3$ is a cyano group, by reacting a compound of the formula (5):

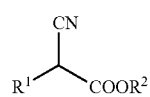

wherein $R^1$ is an amino group protected with a group removed by hydrogenolysis or a tert-butoxycarbonylamino group, and $R^2$ is an ethyl group optionally substituted with one or two methyl group(s) at α-position, provided that $R^2$ is not a tert-butyl group when $R^1$ is a tert-butoxycarbonylamino group, with (−)-menthyl chloroacetate.

The present invention also provides with a process for producing a succinic acid diester derivative of the formula (1a), which is a compound of the formula (1) wherein $R^3$ is a carbamoyl group, comprising a step of converting a cyano group of the succinic acid diester derivative (1b), which is a compound (1) wherein $R^3$ is a cyano group, into a carbamoyl group.

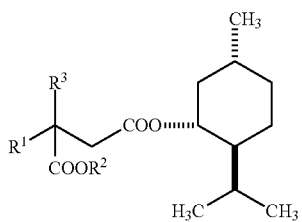

(1a): $R^3$=carbamoyl
(1b): $R^3$=cyano

The present invention also provides with a process for producing a succinic acid diester derivative of the formula (2), comprising a step of recrystallizing a succinic acid diester derivative (1a), which is a compound (1) wherein $R^3$ is a carbamoyl group, from acetone.

The present invention also provides with a novel process for producing a ranirestat, comprising a step of preparing a succinimide derivative of the formula (3) by reacting a compound of the formula (2) with a base, and a step of converting the succinimide derivative into ranirestat.

In detail, a novel process for producing a ranirestat, comprising
1) a step of preparing a succinimide derivative of the formula (3) by reacting a compound of the formula (2) with a base;
2) a step of converting $R^1$ (an amino group protected with a group removed by hydrogenolysis or a tert-butoxycarbonylamino group) of the succinimide derivative (3) into an amino group;
3) a step of converting the amino group of the product in the above step 2) into a pyrrol-1-yl group;
4) a step of converting the pyrrol-1-yl group of the product in the above step 3) into a 2-trichloroacetylpyrrol-1-yl group; and
5) a step of preparing ranirestat by reacting the product of the above step 4) with 4-bromo-2-fluorobenzylamine,
is provided.

The present invention also provides with a process for producing a ranirestat using the compound of the formula (1) or (2) as a synthetic intermediate or a starting compound.

The present invention also provides with a use of the compound of the formula (1) or (2) as a synthetic intermediate or a starting compound for producing a ranirestat.

Effects of the Invention

According to the present invention, it is possible to synthesize the optically active succinimide derivative of the formula (3) without using cinchonidine as an agent of optical resolution. Further, the process of the present invention is cost effective and suitable for production in manufacturing scale since a special kind of starting material or solvent is unnecessary.

BEST MODE OF CARRYING OUT THE INVENTION

A compound of the present invention may exist as a hydrate and/or a solvate and these hydrate and/or solvate are also included in the compounds of the present invention. Moreover, there are one or more asymmetric carbon(s) in a molecule and various stereoisomers may exist in the compound of the present invention. Accordingly each stereoisomer, a mixture of stereoisomers and a racemic mixture thereof are also included in the present invention unless the stereochemistry is clearly specified.

Terms in the present specification are explained below.

"Amino group protected with a group removed by hydrogenolysis" is an amino group protected with a protecting group which is commonly used in the field of peptide synthesis and removed by hydrogenolysis and for example, a benzyloxycarbonylamino group a benzene ring of which is optionally substituted, a benzylamino group a benzene ring of which is optionally substituted, a benzhydrylamino group a benzene ring of which is optionally substituted, and a tritylamino group a benzene ring of which is optionally substituted are exemplified. Moieties of benzene rings in these benzyloxycarbonylamino group, benzylamino group, benzhydrylamino group and tritylamino group may be substituted with one to three atom(s) or group(s) selected from halogen, $C_{1-6}$ alkyl, $C_{1-6}$ alkoxy and a nitro group. For example, a benzyloxycarbonylamino group, a 4-nitrobenzyloxycarbonyl group, a 4-chloro benzyloxycarbonylamino group, a benzylamino group, a 4-methylbenzylamino group, a 4-methoxybenzylamino group, a 2,4-dimethoxybenzylamino group, a benzhydrylamino group and a tritylamino group are exemplified.

Examples of the preferred groups include a benzyloxycarbonylamino group a benzene ring of which is optionally substituted (e.g., a benzyloxycarbonylamino group, 4-nitrobenzyloxycarbonylamino group and 4-chlorobenzyloxycarbonylamino group) and the benzyloxycarbonylamino group is most preferred.

"Ethyl group optionally substituted with one or two methyl group(s) at α-position" includes an alkyl group wherein one or two methyl group(s) are substituted at α-position of the said ethyl group as well as an ethyl group, and specifically an ethyl group, an isopropyl group and a tert-butyl group are included.

Among them, an ethyl group and a tert-butyl group are preferred.

Also in a compound of the formula (1), (2) or (3), a combination wherein $R^1$ is an amino group protected with a group removed by hydrogenolysis or a tert-butoxycarbonylamino group, and $R^2$ is an ethyl group or a tert-butyl group is preferred, and a combination wherein $R^1$ is a benzyloxycarbonylamino group or a tert-butoxycarbonylamino group and $R^2$ is an ethyl group or a tert-butyl group is more preferred. However, $R^2$ cannot be a tert-butyl group when $R^1$ is a tert-butoxycarbonylamino group in every preferable case.

Examples of "alkali metal alkoxide" include sodium methoxide, sodium ethoxide, sodium isopropoxide, sodium tert-butoxide, sodium tert-pentoxide, potassium tert-butoxide, lithium tert-butoxide and the like.

The succinic acid diester and succinimide derivatives can be prepared according to a method shown in the reaction scheme below:

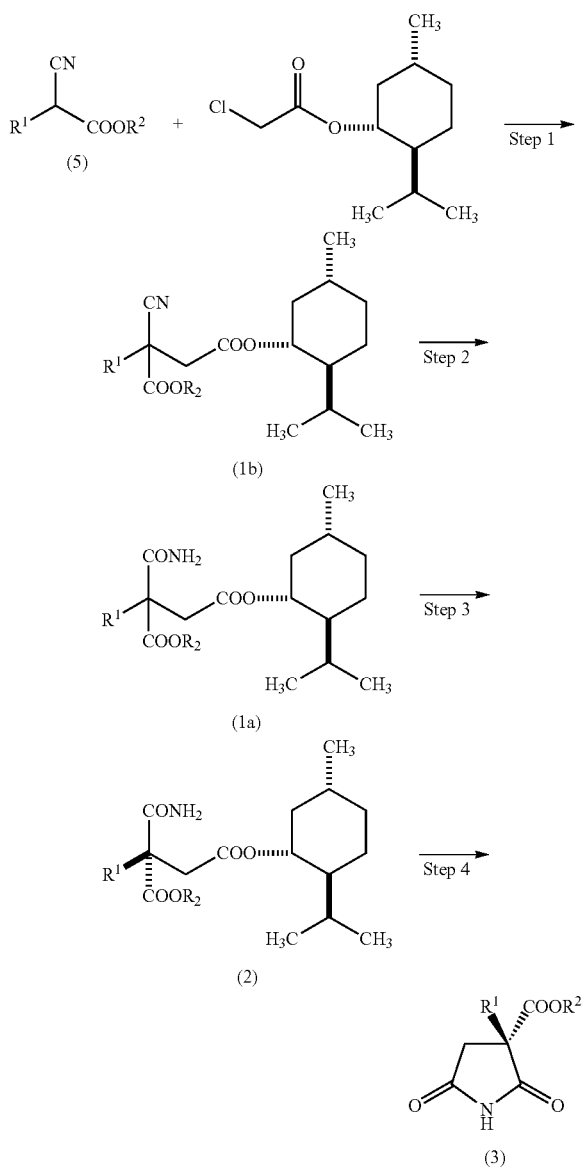

wherein $R^1$ and $R^2$ are the same as described above.

(Step 1)

A compound of the formula (5) can be prepared by protecting an amino group of 2-amino-2-cyanoacetic acid ester, which is prepared according to a method described in Chem. Ind. (London), 1980, 541-542, by a common method.

(−)-Menthyl chloroacetate (MCA) can be prepared by reacting monochloroacetic acid with (−)-menthol under the presence of an acid catalyst in a solvent such as toluene and removing water through azeotropic distillation using a Dean-Stark apparatus.

The reaction of the compound of the formula (5) with MCA is usually carried out under the presence of a base in a suitable solvent. Examples of the solvent include toluene, tetrahydrofuran, dioxane, acetone, dimethylformamide and the like. Examples of the base include sodium carbonate, potassium carbonate, sodium bicarbonate, potassium bicarbonate, sodium methoxide, sodium ethoxide, potassium tert-butoxide and the like. The reaction temperature is usually at −10° C. to 100° C.

(Step 2)

A conversion of the compound of the formula (1b) to the compound of the formula (1a) is usually carried out under the presence of a base and hydrogen peroxide in a suitable solvent. Examples of the solvent include acetone, methanol, ethanol, dimethylsulfoxide, water and a mixture thereof. Examples of the base include sodium carbonate, potassium carbonate, sodium bicarbonate, potassium bicarbonate and the like, and a reaction temperature is at about −10° C. to about 80° C., preferably at 30° C. to 50° C.

(Step 3)

The compound of the formula (1a) is a diastereomeric mixture of the objective compound [(2-R)-derivative] and the other diastereomer [(2-S)-derivative] of the formula (2). One recrystallization of the mixture (1a) from acetone gives the objective compound (2) in good yield. An optical purity of the product is also excellent.

(Step 4)

A conversion of the compound of the formula (2) to the compound of the formula (3) is carried out under the presence of sodium alkoxide in a lower alcohol at −30° C. to 0° C.

A compound of the formula (3) [a compound of the formula (3a) in the reaction scheme below] can be converted to a compound of the formula (4) shown in the scheme below:

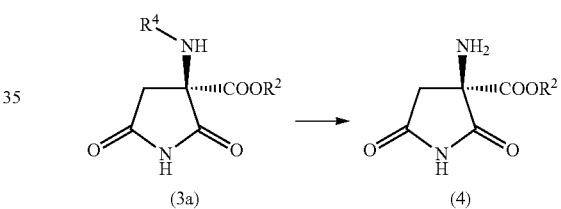

wherein $R^4$ is an amino group protected with a group removed by hydrogenolysis or a tert-butoxycarbonyl group, and $R^2$ is an ethyl group optionally substituted with one or two methyl group(s) at α-position, provided that $R^2$ is not a tert-butyl group when $R^4$ is a tert-butoxycarbonyl group;

When $R^4$ is a group removed by hydrogenolysis, a conversion of the compound of the formula (3a) to the compound of the formula (4) can be carried out by reacting the compound (3a) with hydrogen gas under the presence of a catalyst such as Raney-Ni or palladium-carbon etc. in a suitable solvent, or by reacting the compound (3a) with a hydrogen donor (e.g., ammonium formate) under the presence of a catalyst such as palladium-carbon etc. Examples of the solvent include water, methanol, ethanol, acetic acid, dioxane, tetrahydrofuran and the like. The reaction temperature is usually at about 25° C. to about 80° C. and the reaction is performed under a normal or increased pressure. When $R^4$ is a tert-butoxycarbonyl group or a trityl group, the compound of the formula (4) can be prepared by treating the compound of the formula (3a) with an acid such as trifluoroacetic acid or hydrochloric acid etc. in a suitable solvent.

In a patent or non-patent literature [JP 1993-186472A or J. Med. Chem., 41, 4118 (1998)], it is described that the compounds of the formula (3) and (4) are synthetic intermediates of ranirestat, and the compound of the formula (1) or (2) of the present invention can be utilized as a intermediate or a starting material of ranirestat since the compounds of the formula (3) and (4) can be prepared from the compound of the formula (1) or (2).

EXAMPLES

The present invention is illustrated more in detail below by examples and reference examples, but not construed to be limited to these examples.

Each compound was identified by NMR (400 MHz) spectra and an optical purity was determined by HPLC.

Reference Example 1

Preparation of Ethyl 2-benzyloxycarbonylamino-2-cyanoacetate [Compound (5): $R^1$=benzyloxycarbonylamino, $R^2$=ethyl]

To a mixture of ethyl 2-cyano-2-hydroxyiminoacetate (100 g, 0.704 mol) and water (600 ml), were added a saturated aqueous solution of sodium bicarbonate (200 ml) and sodium hydrosulfite (340 g, 1.96 mol) under ice-cooling, and then benzyloxycarbonyl chloride (144 g, 0.848 mol) was added dropwise under ice-cooling. After the addition was completed, the reaction solution was stirred at 20-30° C. for about 4 hours. Completion of the reaction was confirmed using TLC shown below, precipitated crystals were collected by filtration and washed with sprayed water (50 ml×3). The obtained crystals were recrystallized from ethanol (600 ml), filtered and washed with sprayed ethanol (50 ml×3), dried in airflow at 40° C. to give ethyl 2-benzyloxycarbonylamino-2-cyanoacetate (118.7 g, yield 64.2%).
TLC condition:
Hexane:ethyl acetate:acetic acid=50:50:1, detected by iodine.

Reference Example 2

Preparation of t-butyl 2-benzyloxycarbonylamino-2-cyanoacetate [Compound (5): $R^1$=benzyloxycarbonylamino, $R^2$=t-butyl]

To a mixture of 2-benzyloxycarbonylamino-2-cyanoacetic acid (2.00 g, 8.54 mmol), toluene (20 ml) and t-butyl alcohol (6.33 g, 85.4 mmol), was added trifluoroacetic acid anhydride (7.17 g, 34.2 mmol) dropwise and the solution was stirred for half an hour. The reaction solution was neutralized by adding 10% NaOH aqueous solution (18 g), the organic layer was separated and washed with water three times, dried over sodium sulfate, insoluble materials were filtered and the filtrate was condensed to give t-butyl 2-benzyloxycarbonylamino-2-cyanoacetate (1.67 g, yield 67.4%) as a pale yellow oil.
$^1$H-NMR (CDCl$_3$/ppm, TMS): 1.53 (9H, s), 5.18-5.12 (3H, m), 5.60 (1H, br s), 7.40-7.32 (5H, m).

Reference Example 3

Preparation of Menthyl 2-chloroacetate (MCA)

A mixture of l-(−)-menthol (100 g, 0.640 mol), chloroacetic acid (72.8 g, 0.768 mol), p-toluenesulfonic acid (4.81 g, 0.025 mol) and cyclohexane (480 ml) was heated to 80-85° C. of inner temperature and refluxed for about three hours, while water was azeotropically distilled using Dean-Stark dehydrating apparatus.

When completion of the reaction was confirmed by TLC shown below, the reaction solution was cooled to room temperature, washed with water (250 ml×2), a saturated aqueous solution of sodium bicarbonate (200 ml) and a saturated brine (200 ml). The organic layer was dried over sodium sulfate, insoluble materials were filtered and the filtrate was concentrated in vacuo to give menthyl 2-chloroacetate (129.8 g) as a pale yellow liquid.
TLC condition:
Hexane:ethyl acetate=1:1, detected by phosphomolybdic acid

Example 1

Preparation of Ethyl 2-benzyloxycarbonylamino-2-cyano-3-[(−)-menthyloxycarbonyl]propionate [Compound (1b): $R^1$=benzyloxycarbonylamino, $R^2$=ethyl]

To a mixture of ethyl 2-benzyloxycarbonylamino-2-cyanoacetate (213 g, 0.812 mol), acetone (316 g), powdered potassium carbonate (135 g, 0.974 mol) and potassium iodide (27.0 g, 0.162 mol), was added a solution of MCA (189 g, 0.812 mol) in acetone (160 g) dropwise at 10-20° C. and the mixture was stirred at the same temperature overnight. The reaction solution was concentrated in vacuo and the residue was diluted with 3M-HCl (500 ml). It was extracted with toluene (639 ml×2) and the organic layer was washed with water (639 ml×2) and concentrated in vacuo to give ethyl 2-benzyloxycarbonylamino-2-cyano-3-[(−)-menthyloxycarbonyl]propionate (373 g, yield 100%) as a red brown oil. Optical purity of (2R)-derivative: 10.5% d.e.
$^1$H-NMR (CDCl$_3$, δ/ppm, TMS): 0.70-1.93 (21H, m), 3.18 (1H, dd, J=16.3, 6.1 Hz), 3:59 (1H, d, J=15.9 Hz), 4.37 (2H, m), 4.70 (1H, dq, J=16.6, 4.4 Hz), 5.16 (2H, m), 6.36 (1H, s), 7.34-7.39 (5H, m).

Example 2

Preparation of Ethyl 2-benzyloxycarbonylamino-2-carbamoyl-3-[(−)-menthyloxycarbonyl]propionate [Compound (1a): $R^1$=benzyloxycarbonylamino, $R^2$=ethyl]

A mixture of sodium carbonate (80.1 g, 0.756 mol), water (1010 ml), ethyl 2-benzyloxycarbonylamino-2-cyano-3-[(−)-menthyloxycarbonyl]propionate (192 g, 0.420 mol) and acetone (963 ml) was stirred at 13° C. 30% Hydrogen peroxide solution (300 ml) was added dropwise under cooling with water, and the mixture was heated to 38-42° C. (inner temperature) and stirred for about four hours.

When completion of the reaction was confirmed by TLC shown below, the reaction solution was cooled to room temperature and water (248 ml) was added. The precipitated crystals were filtered, washed with water (700 filtered again and washed with sprayed water (160 ml). The crystals were washed with hexane (1100 ml), filtered and washed with sprayed hexane (300 ml).

The crystals were dried at 60° C. to give ethyl 2-benzyloxycarbonylamino-2-carbanmoyl-3-[(−)-menthyloxycarbonyl]propionate (177 g) as a white crystal. mp. 139° C. yield 88.4%, HPLC (area) 97.2%. Optical purity of (2R)-derivative: 12.2% d.e.

¹H-NMR (CDCl₃, δ/ppm, TMS): 0.69-1.92 (21H, m), 3.43-3.54 (2H, m), 4.24 (2H, q, J=6.8 Hz), 4.65 (1H, tt, J=10.9, 4.7), 5.05-5.16 (2H, m), 5.57 (1H, s br), 6.33 (1H, s br), 6.52 (1H, s br), 7.32-7.36 (5H, m).
TLC condition:
  Ethyl acetate:toluene=1:3, detected by phosphomolybdic acid
HPLC condition:
  Column: CAPCELL PAK C18 UG120(4.6 mm I.D.×250 mm)
  Mobile phase:acetnitrile:0.05% TFA aq.=3:2
  Detection: UV 215 nm
  Range of Analyzed Area: 40 min Example 3

Preparation of ethyl (2R)-2-benzyloxycarbony-lamino-2-carbamoyl-3-[(−)-menthyloxycarbonyl] propionate [Compound (2): R¹=benzyloxycarbonylamino, R²=ethyl]

Acetone (750 g) was added to ethyl 2-benzyloxycarbony-lamino-2-carbamoyl-3-[(−)-menthyloxycarbonyl]propionate (150 g, 0.315 mol) and the mixture was heated to 40° C., the solid was dissolved and then the solution was gradually cooled. It was placed to be matured at 10° C. overnight and then stirred at 5° C. for about an hour. The crystals were filtered, washed with sprayed cold acetone (50 ml×2) and dried in airflow at 60° C. to give ethyl (2R)-2-benzyloxycarbonylamino-2-carbamoyl-3-[(−)-menthyloxycarbonyl]propionate (57.9 g). mp. 124° C., yield 38.6%: optical purity (HPLC) 98.8% d.e.

About 200 g of acetone was evaporated from the mother liquid, the residue was placed at room temperature (about 10° C.) for two days and nights and the precipitated crystals were filtered and dried to give 2-benzyloxycarbonylamino-2-carbamoyl-3-[(−)-menthyloxycarbonyl]propionate (44.8 g), optical purity of which was 2.3% d.e.

The recovered 2-benzyloxycarbonylamino-2-carbamoyl-3-[(−)-menthyloxycarbonyl]propionate can be used as a material for recrystallization and the yield will be 57.9/(150-44.8)×100=55.0% if the recovery is taken into consideration.

The mother liquid was concentrated to give (2S)-2-benzyloxycarbonylamino-2-carbamoyl-3-[(−)-menthyloxycarbonyl]propionate (42.2 g), the optical purity of which was 80.3% d.e.
HPLC condition:
  Column: DAICEL Chiralpak AD 250 mm×4.6 mm I.D.
  Mobile phase:n-Hexane:IPA=8:2
  Column temperature: constant temperature at about 30° C.
  Flow rate: 1 ml/min
  Detection: UV 210 nm
  Range of Analyzed Area: 30 min Example 4

Preparation of (2R)-2-benzyloxycarbonylamino-2-ethoxycarbonylsuccinimide [Compound (3), R¹=benzyloxycarbonylamino, R²=ethyl]

20% Ethanol solution of sodium ethoxide (40.5 g, 119 mmol) was diluted with ethanol (377 ml) and cooled to −4° C. to −7° C. (2R)-2-Benzyloxycarbonylamino-2-carbamoyl-3-[(−)-menthyloxycarbonyl]propionate (optical purity: 98.8% d.e., 47.1 g, 98.8 mmol) was added at the same temperature and the mixture was stirred at the same temperature for 3.5 hours.

When completion of the reaction was confirmed by TLC shown below, concentrated hydrochloric acid (19.4 g) was added and the solution was adjusted to about pH 2. After evaporation of ethanol in vacuo from the reaction solution, water (184 ml) was added to the residue, the solution was extracted with ethyl acetate (141 ml) and the organic layer was washed with saturated brine (141 ml), dried over sodium sulfate and ethyl acetate was evaporated in vacuo. The residue was crystallized by addition of hexane (141 ml) and the crystals were filtered and dried to give (2R)-2-benzyloxycarbonylamino-2-ethoxycarbonylsuccinimide (27.4 g). yield 86.6%, optical purity: 99.4% e.e.
TLC condition:
  Ethyl acetate:toluene=1:3, detected by phosphomolybdic acid
HPLC condition (optical purity):
  Column: Chiralpak AS 250 mm×4.6 mm I.D.
  Mobile phase: hexane:ethanol=8:2
  Column temperature: constant temperature at about 40° C.
  Flow rate: 1 ml/min
  Detection: UV 215 nm
  Range of Analyzed Area 30 min Example 5

Preparation of (2R)-2-amino-2-ethoxycarbonylsuccinimide [compound (4), R²=ethyl]

(2R)-2-Benzyloxycarbonylamino-2-ethoxycarbonylsuccinimide (24.4 g, 76.2 mmol) in ethanol (73.2 ml) was heated at 60° C. to be dissolved and 5% Pd—C (2.71 g) and water (2.17 g) were added at 30-40° C. of inner temperature. After the atmosphere was substituted with nitrogen gas, hydrogen gas was introduced and the mixture was stirred at 30-40° C. for about 33 hours. When completion of the reaction was confirmed by HPLC, the reaction solution was filtered, the insoluble materials were washed with sprayed ethanol (20 ml×2) and the filtrate was concentrated. The resulting crystals were recrystallized from ethanol (24.4 ml) and the precipitated crystals were filtered, washed with sprayed ethanol (15 ml) and dried in vacuo at room temperature to give (2R)-2-amino-2-ethoxycarbonylsuccinimide (12.3 g). Yield 86.7%, HPLC 99.7%, Optical purity 100% e.e.

The optical purity and related products were analyzed by HPLC under the following condition;
HPLC condition (optical purity)
  Column: CROWNPAK CR(+), 4.6 mm I.D×15 cm (Daicel Chemical Industries, LTD)
  Mobile phase: aqueous perchloric acid solution, pH 1.0
  Column temperature: constant temperature at about 40° C.
  Flow rate: 0.45 ml/min
  Detection: UV 196 nm
  Range of Analyzed Area: about three times as long as the retention time of (2R)-2-amino-2-ethoxycarbonylsuccinimide
HPLC condition (related product)
  Column: Xterra MS C18, Waters Co., Ltd.
  Mobile phase: mobile phase A: phosphate buffer
  mobile phase B: methanol
  Elution condition: concentration gradient was controlled by mixing the mobile phase A and B in the following ratio;

| lapse time after injection (min.) | mobile phase A (%) | mobile phase B (%) |
|---|---|---|
| 0-10 | 85 | 15 |
| 10-20 | 85→60 | 15→40 |
| 20-40 | 60 | 40 |
| 40-45 | 60→85 | 40→15 |
| 45-60 | 85 | 15 |

Column temperature: constant temperature at about 40° C.
Flow rate: 0.6 ml/min
Detection: UV 218 nm
Range of Analyzed Area: about 40 min Example 6

Preparation of Ethyl 2-(tert-butoxycarbonylamino)-2-cyano-3-[(−)menthyloxycarbonyl]propionate [Compound (1b): $R^1$=tert-butoxycarbonylamino, $R^2$=ethyl]

Ethyl 2-(tert-butoxycarbonylamino)-2-cyanoacetate (1.20 g, 526 mmol) prepared in the same manner as Reference Example 1, acetone (2.3 ml), powdered potassium carbonate (872 mg, 6.31 mmol) and potassium iodide (175 mg, 1.05 mmol) were mixed, a solution of menthyl chloroacetate (1.22 g, 5.26 mmol) dissolved in acetone (1.1 ml) was added dropwise thereto at 10-20° C., and the mixture was stirred at the same temperature overnight. Insoluble materials were removed by filtration, the filtrate was concentrated in vacuo and toluene was added to the residue. The organic layer was washed with water and concentrated in vacuo to give ethyl 2-(tert-butoxycarbonylamino)-2-cyano-3-[(−)menthyloxycarbonyl]propionate (1.10 g, yield 49.3%) as a yellow oil.

$^1$H-NMR (CDCl$_3$, δ/ppm, TMS): 1.48 (9H, s), 0.73-1.98 (21H, m), 3.14 (1H, dd, J=15.9, 6.3 Hz), 3.50 (1H, s br), 4.38 (2H, tt, J=8.4, 2.8 Hz), 4.72 (1H, td, J=11.0, 4.4 Hz), 6.08 (1H, s br).

Example 7

Preparation of Ethyl 2-(tert-butoxycarbonylamino)-2-carbamoyl-3-[(−)-menthyloxycarbonyl]propionate [Compound (1a): $R^1$=tert-butoxycarbonylamino, $R^2$=ethyl]

Potassium carbonate (586 mg, 4.24 mmol), water (2.5 ml), ethyl 2-(tert-butoxycarbonylamino)-2-cyano-3-[(−)-menthyloxycarbonyl]propionate (1.00 g, 2.46 mmol) and acetone (5 ml) were mixed and 30% aqueous hydrogen peroxide solution (0.8 ml) was added dropwise under cooling with water. Then the mixture was heated at 10-30° C. of inner temperature and stirred for about 4 hours. The precipitated crystals were filtered and washed with sprayed water.

It was dried in airflow at 60° C. overnight to give ethyl 2-(tert-butoxycarbonylamino)-2-carbamoyl-3-[(−)-menthyloxycarbonyl]propionate (802 mg, yield 73.3%). Optical purity was 10.7% d.e.

$^1$H-NMR (CDCl$_3$, δ/ppm, TMS): 1.43 (9H,$), 0.72-1.93 (21H, m), 3.45 (2H,$), 4.26 (2H, m), 4.68 (1H, tt, J=10.9, 3.9 Hz), 5.51 (1H, s br), 6.25 (1H, s br), 6.41 (1H, s br).

Example 8

Preparation of Ethyl (2R)-2-(tert-butoxycarbonylamino)-2-carbamoyl-3-[(−)-menthyloxycarbonyl] propionate [Compound (2): $R^1$=tert-butoxycarbonylamino, $R^2$=ethyl]

Ethyl 2-(tert-butoxycarbonylamino)-2-carbamoyl-3-[(−)-menthyloxycarbonyl]propionate (737 mg, 1.67 mmol) was dissolved in acetone (3.69 g) and the solution was placed at 5-10° C. The precipitated crystals were filtered to give ethyl (2R)-2-(tert-butoxycarbonylamino)-2-carbamoyl-3-[(−)-menthyloxycarbonyl]propionate (88 mg) as a white crystal. mp. 176° C., optical purity: 82.6% d.e.

$^1$H-NMR (CDCl$_3$, δ/ppm, TMS): 1.43 (9H, s), 0.73-1.94 (21H, m), 3.45 (2H, s), 4.27 (2H, q, J=6.9 Hz), 4.68 (1H, td, J=11.0, 4.3 Hz), 6.22 (1H, s br), 5.38 (1H, s br), 6.34 (1H, s br).

Example 9

Preparation of t-Butyl 2-benzyloxycarbonylamino-2-cyano-3-[(−)-menthyloxycarbonyl]propionate [compound (1b): $R^1$=benzyloxycarbonylamino, $R^2$=t-butyl]

t-Butyl 2-benzyloxycarbonylamino-2-cyanoacetate (1.65 g, 5.68 mmol), powdered potassium carbonate (943 mg, 6.82 mmol), potassium iodide (189 mg, 1.14 mmol) and acetone (5.0 ml) were mixed, MCA (1.32 g, 5.68 mmol) was added under ice-cooling and the mixture was stirred at room temperature. When completion of the reaction was confirmed, the reaction solution was concentrated, 3N—HCl was added thereto and extracted with toluene. The organic layer was washed with water (×2), dried over sodium sulfate and insoluble materials were filtered. The organic layer was concentrated to give t-butyl 2-benzyloxycarbonylamino-2-cyano-3-[(−)-menthyloxycarbonyl]propionate (2.18 g, yield 78.9%) as a red-brown oil.

$^1$H-NMR (CDCl$_3$/ppm, TMS): 1.92-0.69 (27H, m), 3.13 (1H, d, J=16.6 Hz), 3.59 (1H, t, J=15.2 Hz), 4.70 (1H, tdd, J=10.9, 4.5, 2.1 Hz), 5.22-5.09 (2H, m), 6.30 (1H, br s), 7.38-7.34 (5H, m).

Example 10

Preparation of t-Butyl 2-benzyloxycarbonylamino-2-carbamoyl-3-[(−)-menthyloxycarbonyl]propionate [compound (1a): $R^1$=benzyloxycarbonylamino, $R^2$=t-butyl]

t-Butyl 2-benzyloxycarbonylamino-2-cyano-3-[(−)-menthyloxycarbonyl]propionate (2.00 g, 4.11 mmol) and acetone (10 ml) were mixed and an aqueous solution of potassium carbonate (566 mg, 5.34 mmol) in water (5.0 ml) was added thereto. Further, 30% aqueous hydrogen peroxide solution (1.6 ml) was added dropwise and the mixture was stirred for about 6 hours. When completion of the reaction was confirmed, water was added and the precipitated crystals were filtered, washed with sprayed water and hexane to give t-butyl 2-benzyloxycarbonylamino-2-carbamoyl-3-[(−)-menthyloxycarbonyl]propionate (950 mg, yield 45.8%) as a pale yellow crystal. Optical purity of (2R)-derivative was 7.4% d.e.

$^1$H-NMR (CDCl$_3$/ppm, TMS): 1.94-0.70 (27H, m), 3.45 (2H, d, J=10.7 Hz), 4.67 (1H, tdd, J=10.9, 4.3, 1.7 Hz), 5.14-5.07 (2H, m), 5.41 (1H, br s), 6.22 (1H, br s), 6.48 (1H, br s), 7.38-7.30 (5H, m).

Example 11

Preparation of t-Butyl (2R)-2-benzyloxycarbony-lamino-2-carbamoyl-3-[(−)-menthyloxycarbonyl] propionate [compound (2): $R^1$=benzyloxycarbonylamino, $R^2$=t-butyl]

t-Butyl 2-benzyloxycarbonylamino-2-carbamoyl-3-[(−)-menthyloxycarbonyl]propionate (500 mg) was dissolved in acetone (2.5 g) under heating and placed in a freezer overnight. The precipitated crystals were filtered and dried to give t-butyl (2R)-2-benzyloxycarbonylamino-2-carbamoyl-3-[(−)-menthyloxycarbonyl]propionate (44 mg, yield 8.8%) as a white crystal. Optical purity of (2R)-derivative: 79.1% d.e.

$^1$H-NMR (CDCl$_3$/ppm, TMS): 1.93-0.69 (27H, m), 3.43 (2H, s), 4.66 (1H, td, J=10.9, 4.3, Hz), 5.14-5.05 (2H, m), 5.41 (1H, br s), 6.21 (1H, br s), 6.47 (1H, br s), 7.34-7.32 (5H, m).

Example 12

Preparation of (3R)-2'-(4-bromo-2-fluorobenzyl) spiro[pyrrolidin-3,4'(1'H)-pyrrolo[1,2-a]pyrazin]-1', 2,3',5(2'H)-tetraone 2,5-Dimethoxytetrahydrofuran (7.4 g) and 2.5% aqueous acetic acid (50 g) were added to ethyl (2R)-2-amino-2-ethoxycarbonylsuccinimide (10 g) and the mixture was stirred at 70° C. for 1.5 hours. The reaction solution was cooled and insoluble materials were dissolved by addition of ethyl acetate (50 ml) and stirring. The mixture was placed for a while and the organic layer was separated from the aqueous layer, washed with brine, dried over magnesium sulfate and filtered. The filtrate was concentrated in vacuo, diisopropylether (37 g) and ethyl acetate (9.2 g) were added to the residue and diisopropylamine (6.2 g) was added and the mixture was stirred at 0-5° C. of inner temperature. The precipitated crystals were filtered, washed with diisopropylether and dried to give (2R)-2-ethoxycarbonyl-2-(pyrrol-1-yl)succinimide diisopropylamine salt (yield 88%).

To a suspension of (2R)-2-ethoxycarbonyl-2-(pyrrol-1-yl) succinimide diisopropylamine salt (20.0 g) in ethyl acetate (100 ml), was added 20% aqueous sulfuric acid (16 ml) and the salt was dissolved. The solution was placed after stirring and the organic layer was separated with the aqueous layer. The organic layer was separated with the aqueous layer again after brine was added to the organic solution, and the mixture was stirred and placed. The organic layer was concentrated in vacuo, ethyl acetate (50 ml) and trichloroacetyl chloride (32.3 g) were added to the residue and the mixture was stirred under reflux for 6 hours. The reaction solution was cooled, ethyl acetate (134 ml) was added thereto and it was washed with brine, aqueous solution of sodium bicarbonate, 5% aqueous sulfuric acid and brine successively. The organic layer was concentrated in vacuo, N-methylpyrrolidone (26 ml) and ethyl acetate (6.7 ml) were added and the residue was dissolved. The solution was cooled and diisopropylamine (9 g) was added thereto and the mixture was stirred. 4-Bromo-2-fluorobenzylamine (24.2 g) was added dropwise under ice-cooling and the mixture was stirred at 0-5° C. for 18 hours. Ethyl acetate (266 ml) was added to the reaction solution and it was washed with 5% aqueous sulfuric acid, aqueous solution of sodium bicarbonate, 5% aqueous sulfuric acid and brine successively. The organic layer was concentrated in vacuo, ethanol (100 ml) was added to the residue and it was dissolved under heating to reflux. Ethanol (33 ml) was evaporated, the concentrated solution was cooled with ice-water and the precipitated crystals were filtered and washed with ethanol The resulting wet crystals were recrystallized from isopropanol (124 ml and 180 ml) twice to give (3R)-2'-(4-bromo-2-fluorobenzyl)spiro[pyrrolidin-3,4'(1'H)-pyrrolo[1, 2-a]pyrazin]-1',2,3',5(2H)-tetraone (yield 58%).

Comparative Example 1

Preparation of Ethyl 2-benzyloxycarbonylamino-3-[2-(+)-bornyloxycarbonyl]-2-carbamoylpropionate

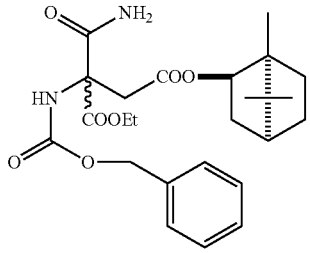

(+)-Bornyl chloroacetate [obtained from (+)-borneol in the same manner as Reference Example 3 above] and ethyl 2-benzyloxycarbonylamino-2-cyanoacetate were reacted in acetone as a solvent in the same manner as Example 1 to give ethyl 2-benzyloxycarbonylamino-3-[2-(+)-bornyloxycarbonyl]-2-cyanopropionate. The resulting diester of the cyano derivative was converted to an amido derivative using hydrogen peroxide in the same manner as Example 2 to give ethyl 2-benzyloxycarbonylamino-3-[2-(+)-bornyloxycarbonyl]-2-carbamoylpropionate as a white crystal. mp. 105-106° C.

$^1$H-NMR (CDCl$_3$, δ/ppm, TMS): 0.75-1.91 (19H, m), 3.49-3.54 (2H, m), 4.27 (2H, m), 4.88 (1H, tt, J=10.9, 4.6 Hz), 5.11 (2H, s), 5.56 (1H, s br), 6.34 (1H, s br), 6.52 (1H, s br), 7.32-7.35 (5H, m).

Comparative Example 2

Preparation of Ethyl 2-benzyloxycarbonylamino-2-carbamoyl-3-[3-(+)-isopinocampheyloxycarbonyl] propionate

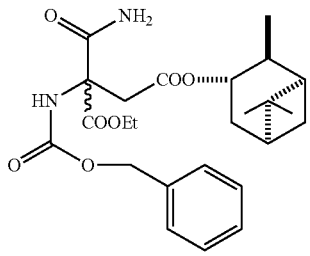

(+)-Isopinocamphenyl chloroacetate [obtained from (+)-isopinocampheol in the same manner as Reference Example 3 before] and ethyl 2-benzyloxycarbonylamino-2-cyanoacetate were reacted in acetone as a solvent in the same manner as Example 1 to give ethyl 2-benzyloxycarbonylamino-2-cyano-3-[3-(+)-isopinocampheyloxycarbonyl]propionate. The resulting diester of the cyano derivative was converted to an amido derivative using hydrogen peroxide in the same manner as Example 2 to give ethyl 2-benzyloxycarbony-lamino-2-carbamoyl-3-[3-(+)-isopinocampheyloxycarbo-nyl]propionate as a white crystal. mp. 89-96° C.

$^1$H-NMR (CDCl$_3$, δ/ppm, TMS): 0.87-2.55 (19H, m), 3.44-3.55 (2H, m), 4.23-4.32 (2H, m), 5.02 (1H, dt, J=12.6, 4.8 Hz), 5.11 (2H, s), 5.69 (1H, s br), 6.39 (1H, s br), 6.54 (1H, s br), 7.31-7.36 (5H, m).

Comparative Test
(1) Solvent Effects

The recrystallization solvent of Example 3 was changed from acetone to toluene, ethyl acetate, tetrahydrofuran, ethanol, isopropyl ether, methyl ethyl ketone or cyclohexyl methyl ether and ethyl 2-benzyloxycarbonylamino-2-carbamoyl-3-[(−)-menthyloxycarbonyl]propionate (a compound of Example 2) was recrystallized but it was unsuccessful to separate a compound of (2R) derivative of Example 3 in each case.

(2) Recrystallization of ethyl 2-benzyloxycarbonylamino-3-[2-(+)-bornyloxycarbonyl]-2-carbamoylpropionate (Comparative Example 1)

In order to separate a diastereomer of the Comparative Example, recrystallization was carried out in acetone, aqueous acetone, methanol, aqueous methanol, acetonitrile, aqueous acetonitrile or ethyl acetate but an optical purity of the resulting diester was about 0% d.e. in each case.

(3) Recrystallization of ethyl 2-benzyloxycarbonylamino-2-carbamoyl-3-[4-(+)-isopinocampheyloxycarbonyl]propionate (Comparative Example 2)

In order to separate a diastereomer of the Comparative Example, recrystallization was carried out in acetone, aqueous acetone, methanol, aqueous methanol, acetonitrile or aqueous acetonitrile but an optical purity of the resulting diester was about 0% d.e. in each case.

As described above, effect of the compounds and methods in the present invention is remarkably characteristic.

INDUSTRIAL APPLICABILITY

The intermediates and method for preparing the same can be used for producing ranirestat which is now under development as an agent for treating diabetes complications.

The invention claimed is:

1. A process for preparing (3R)-2'-(4-bromo-2-fluorobenzyl)spiro[pyrrolidin-3,4'(1'H)-pyrrolo[1,2-a]pyrazin]-1',2,3',5(2'H)-tetraone comprising the following steps:

1) a step in which a compound of the formula (2):

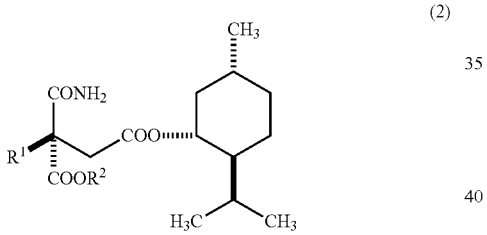

(2)

wherein R' is a) an amino group having a protecting group which can be removed by hydrogenolysis or b) a tert-butoxycarbonylamino group, and $R^2$ is an ethyl group optionally substituted with one or two methyl group(s) at α-position, provided that $R^2$ is not a tert-butyl group when R' is a tert-butoxycarbonylamino group,
is reacted with a base to prepare a succinimide derivative of the formula (3):

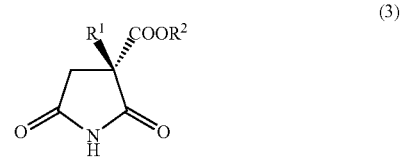

(3)

wherein R' is a) an amino group having a protecting group which can be removed by hydrogenolysis or b) a tert-butoxycarbonylamino group, and $R^2$ is an ethyl group optionally substituted with one or two methyl group(s) at α-position, provided that $R^2$ is not a tert-butyl group when $R^1$ is a tert-butoxycarbonylamino group;

2) a step of converting $R^1$ (an amino group having a protecting group which can be removed by hydrogenolysis or a tert-butoxycarbonylamino group) of the succinimide derivative (3) into an amino group;

3) a step of converting the amino group of the product resulting from the above step 2) into a pyrrol-1-yl group;

4) a step of converting the pyrrol-1-yl group of the product resulting from the above step 3) into a 2-trichloroacetylpyrrol-1-yl group; and (5) a step of preparing (3R)-2'-(4-bromo-2-fluorobenzyl) spiro[pyrrolidin-3,4' (1'H)-pyrrolo[1,2-a]pyrazin]-1',2, 3',5(2'H)-tetraone by reacting the product resulting from the above step 4) with 4-bromo-2-fluorobenzylamine.

2. The process according to claim 1, wherein $R^1$ is a benzyloxycarbonylamino group or a tert-butoxycarbonylamino group, and $R^2$ is an ethyl group.

* * * * *